( 12 ) United States Patent
Saito et al.

(10) Patent No.: US 9,618,526 B2
(45) Date of Patent: Apr. 11, 2017

(54) AUTOMATED ANALYZER (71) Applicant: HITACHI HIGH-TECHNOLOGIES CORPORATION, Minato-ku, Tokyo (JP)

(72) Inventors: Yoshiaki Saito, Hitachinaka (JP); Yoichi Aruga, Hitachinaka (JP); Toshihide Orihashi, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 81 days.

(21) Appl. No.: 14/413,578

(22) PCT Filed: Jul. 8, 2013

(86) PCT No.: PCT/JP2013/068582
§ 371 (c)(1),
(2) Date: Jan. 8, 2015

(87) PCT Pub. No.: WO2014/017275
PCT Pub. Date: Jan. 30, 2014

(65) Prior Publication Data
US 2015/0153370 A1 Jun. 4, 2015

(30) Foreign Application Priority Data

Jul. 25, 2012 (JP) .................. 2012-164300

(51) Int. Cl.
*G01N 35/10* (2006.01)
*G01N 1/38* (2006.01)
(52) U.S. Cl.
CPC ........... *G01N 35/1004* (2013.01); *G01N 1/38* (2013.01); *G01N 2035/1032* (2013.01)

(58) Field of Classification Search
None
See application file for complete search history.

(56) References Cited

U.S. PATENT DOCUMENTS 4,871,682 A * 10/1989 Mazza ..................... G01N 1/38
422/549
5,452,619 A 9/1995 Kawanabe et al.
(Continued)

FOREIGN PATENT DOCUMENTS

JP 2725917 B2 12/1997
JP 2000-55926 A 2/2000
(Continued)

*Primary Examiner* — Sean E Conley
*Assistant Examiner* — Benjamin Whatley
(74) *Attorney, Agent, or Firm* — Mattingly & Malur, PC (57) ABSTRACT An automated analyzer that can effectively reduce contamination of a diluted low-concentration specimen resulting from a high-concentration specimen not being diluted. The automated analyzer includes a specimen nozzle that performs both the function of pipetting a specimen from a specimen container accommodating the specimen and the function of pipetting a specimen diluted by the analyzer, and means for washing the specimen nozzle with a predetermined detergent. When a pipetting process of a high-concentration specimen not being diluted and a pipetting process of a low-concentration specimen diluted by the analyzer are consecutively performed for the same specimen by the specimen nozzle, between the pipetting process of a high-concentration specimen and the pipetting process of a low-concentration specimen, the analyzer performs a washing processing in which the specimen nozzle is washed with the predetermined detergent.

5 Claims, 9 Drawing Sheets (56) References Cited

U.S. PATENT DOCUMENTS

| | | | | |
|---|---|---|---|---|
| 5,610,069 A | * | 3/1997 | Clark | B01F 11/0022 422/562 |
| 6,752,960 B1 | * | 6/2004 | Matsubara | G01N 35/1004 422/552 |
| 2009/0257051 A1 | * | 10/2009 | Kubota | G01N 35/1004 356/237.1 |
| 2012/0318302 A1 | * | 12/2012 | Nakayama | G01N 35/1004 134/26 |
| 2014/0363896 A1 | * | 12/2014 | Suzuki | G01N 35/1004 436/175 |

FOREIGN PATENT DOCUMENTS

| | | | | |
|---|---|---|---|---|
| JP | 2000055926 A | * | 2/2000 | G01N 35/10 |
| JP | 2005-249585 A | | 9/2005 | |
| JP | 2008-209339 A | | 9/2008 | |
| JP | 2009-288052 A | | 12/2009 | |
| JP | 2010019746 A | * | 1/2010 | |
| JP | WO 2013099660 A1 | * | 7/2013 | G01N 35/1004 |

* cited by examiner

AUTOMATED ANALYZER

TECHNICAL FIELD

The present invention relates to an automated analyzer for performing qualitative/quantitative analysis on biological samples such as blood and urine.

BACKGROUND ART

In recent years, as the performance of automated analyzers has been improved, even low-concentration components have become able to be measured by the automated analyzers. Furthermore, as the volume of specimen has been greatly reduced, and as throughput thereof has increased, it is difficult to effectively wash a specimen nozzle within a short time.

Therefore, as a technique for reducing inter-specimen contamination, JP-A-2000-055926 is known in which a processing for washing a specimen nozzle is performed separately from a general washing processing before a new specimen is pipetted.

CITATION LIST

Patent Literature

PTL 1: JP-A-2000-055926

SUMMARY OF INVENTION

Technical Problem

However, in the specimen nozzle, which performs both the function of pipetting a specimen from a specimen container accommodating the specimen and the function of pipetting a specimen diluted by the analyzer, pipetting of a high-concentration specimen in the specimen container and pipetting of a low-concentration specimen diluted by a high factor such as 50-fold are consecutively performed in some cases. In this case, during the operation of directly pipetting the specimen from the specimen container, the influence of contamination may be negligible. However, when pipetting of the high-concentration specimen not being diluted and pipetting of the diluted low-concentration specimen are consecutively performed, the low-concentration specimen is influenced considerably. Furthermore, even though the specimens are pipetted from the same specimen container, if the dilution factor is great, depending on the items to be measured, pipetting of the specimen from the specimen container may exert a considerable influence on the diluted low-concentration specimen.

The present invention has been-made in consideration of the above problem, and an object thereof is to provide an automated analyzer that can effectively reduce contamination of a diluted low-concentration specimen resulting from a high-concentration specimen not being diluted between the same specimens.

Solution to Problem

The present invention for achieving the aforementioned object is an automated analyzer including a specimen nozzle that performs both the function of pipetting a specimen from a specimen container accommodating the specimen and the function of pipetting a specimen diluted by the analyzer, and means for washing the specimen nozzle with a predetermined detergent, in which when a pipetting process of a high-concentration specimen not being diluted and a pipetting process of a low-concentration specimen diluted by the analyzer are consecutively performed for the same specimen by the specimen nozzle, between the pipetting process of the high-concentration specimen and the pipetting process of the low-concentration specimen, the analyzer performs a washing processing in which the specimen nozzle is washed with the predetermined detergent.

Advantageous Effects of Invention

According to the present invention, it is possible to provide an automated analyzer that can effectively reduce contamination of a low-concentration specimen resulting from a high-concentration specimen between the same specimens.

DESCRIPTION OF EMBODIMENTS

Hereinafter, examples of the present invention will be described with reference to drawings. Herein, the present examples are merely one of the embodiments of the present invention, and the present invention is not limited to the embodiments.

Figure 1:
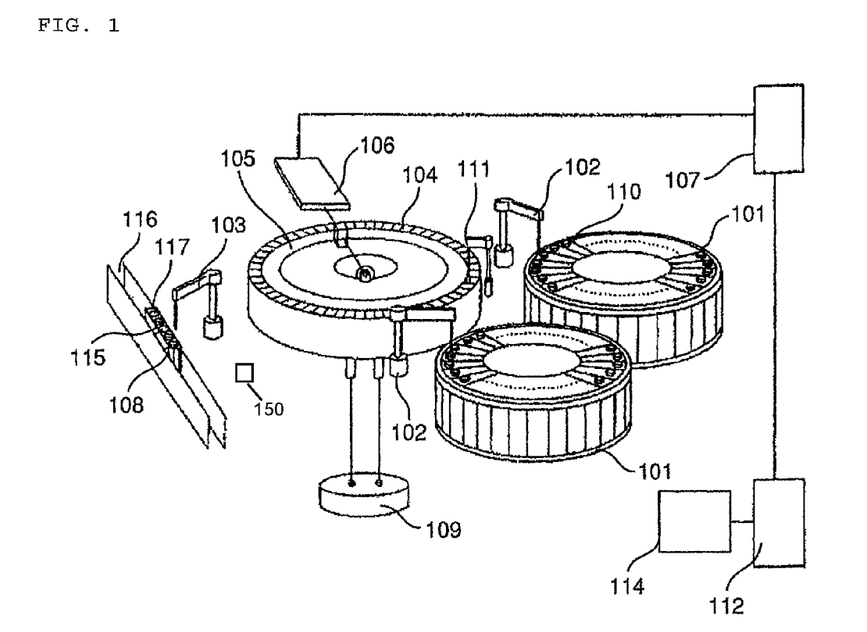
FIG. 1 is a view schematically showing overall configuration of an automated analyzer according to an embodiment of the present invention.

FIG. 1 is a configuration view of an automated analyzer according to an embodiment of the present invention.

The automated analyzer of the present embodiment is mainly configured with a reagent system that includes a reagent dispensing pipetter 102 provided in the vicinity of each of two reagent disks 101 as reagent container storage portions; a sample system that includes a sample dispensing pipetter 103 (specimen nozzle); a reaction system that includes a reaction disk 105 including reaction containers 104; a measurement system that includes a multi-wavelength photometer 106 and an analog/digital (A/D) converter 107; and an operation control system that includes a control portion 112 and a display input portion 114.

A rack 115 equipped with a sample container 117 (specimen container) is transported to a sample aspiration position 108 by a transport portion 116. The sample dispensing pipetter 103 aspirates a sample (also referred to as a "specimen") in the sample container 117, and dispenses the sample in a predetermined volume into the reaction container 104 held in the reaction disk 105.

The reaction container 104, into which the sample liquid has been ejected and dispensed, is moved to a first reagent addition position in the reaction disk 105 which is in communication with a thermostatic bath 109. At this time, the reagent disks 101 performs a rotary operation such that a reagent container 110, which corresponds to a current analysis item, is positioned under the reagent dispensing pipetter 102 held by a hoist arm. Thereafter, a predetermined first reagent aspirated into the reagent dispensing pipetter 102 is added to the reaction container 104 moved to the first reagent addition position. The reaction container 104, to which the first reagent has been added, is moved to the position of a stirring device 111, and initial stirring is performed by the stirring device 111.

A light flux generated from a light source passes through the reaction container 104, of which the content has been stirred, and enters the multi-wavelength photometer 106. Subsequently, an absorbance of the reaction liquid which is the content of the reaction container 104 is detected by the multi-wavelength photometer 106. The detected absorbance signal is supplied to the control portion (computer) 112 via the analog/digital (A/D) converter 107 and an interface, and converted into the concentration of an analysis item as a measurement target in the sample liquid. The display input portion 114 is a graphic user interface (GUI) which is connected to the control portion 112 and displays analysis results or an operation screen. In a state in which the operation screen is displayed on the display input portion 114, if buttons displayed on the operation screen are clicked by using a mouse or the like, the display input portion can be operated.

The reaction container 104 having undergone measurement is moved to the position of a washing mechanism 150, and the liquid in the container is discharged in the position where the reaction container is washed by the washing mechanism. Thereafter, the container is washed with water and used for the next analysis.

Dilution of a specimen will be described. First, the sample dispensing pipetter 103 (specimen nozzle) pipettes a sample, which has not yet been diluted but is to be diluted, and ejects the sample into the reaction container 104. Thereafter, the reagent dispensing pipetter 102 pipettes a diluent in a container installed in the reagent disks 101 and ejects the diluent into the reaction container 104 accommodating the sample which has not yet been diluted. As a result, the high-concentration sample is diluted and becomes a diluted low-concentration sample (also referred to as a "diluted specimen"). The sample dispensing pipetter 103 pipettes the diluted sample and ejects the sample into another reaction container 104. Subsequently, the addition of a reagent thereto, stirring, and the like are performed in the same manner as in the aforementioned operation performed for a sample. Therefore, the sample dispensing pipetter 103 performs both the function of pipetting a sample from the sample container 117 accommodating the sample and the function of pipetting a sample diluted by the analyzer. Herein, the container accommodating the diluent may be provided in a portion other than the reagent disks 101.

The washing processing of the sample dispensing pipetter 103 will be described. In order to prevent inter-specimen contamination, the sample dispensing pipetter 103 is washed with a detergent, water, or the like before pipetting other specimens. The sample dispensing pipetter is washed by a washing mechanism 150.

The control portion 112 controls the respective portions of the analyzer by, for example, controlling driving of the sample dispensing pipetter and controlling the washing processing of the sample dispensing pipetter.

Figure 2:
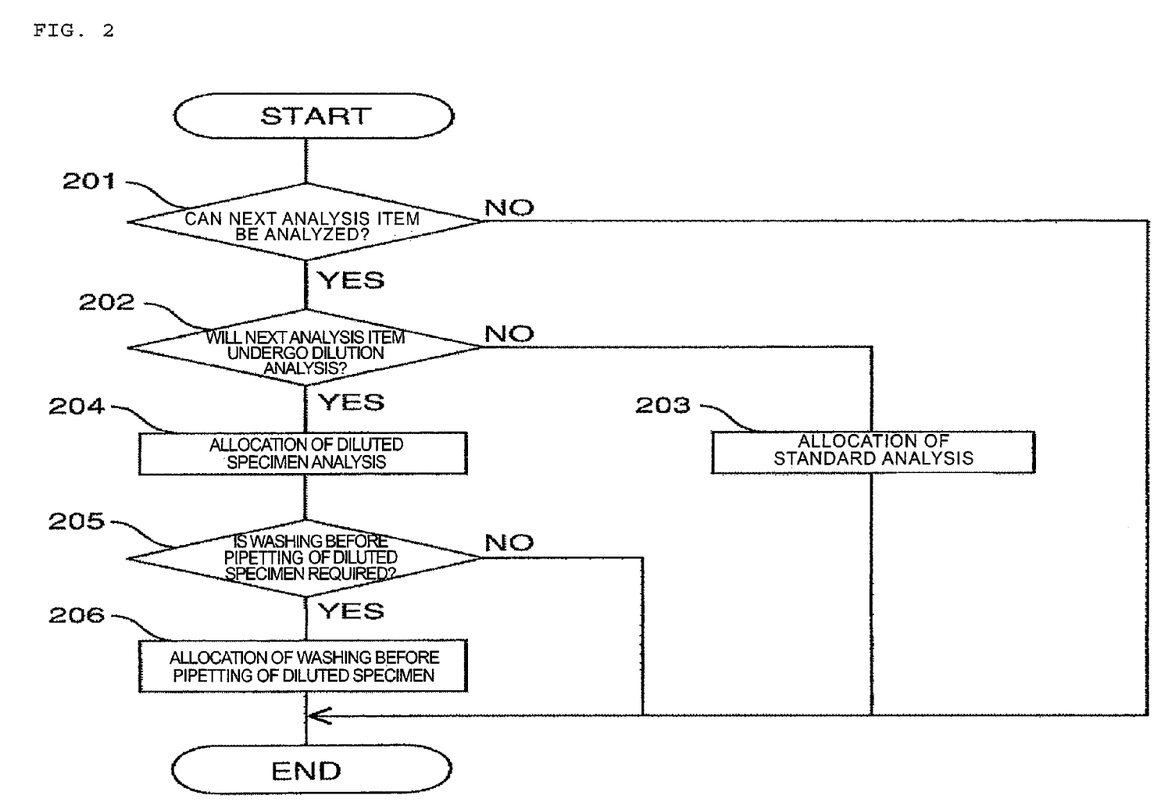
FIG. 2 is a processing flow for programming a washing operation before pipetting of a diluted specimen.

FIG. 2 shows an example of flow of processing of programming a washing operation before pipetting of a diluted specimen. The processing of FIG. 2 is performed whenever there is a request for analysis, regardless of the specimen.

First, the control portion 112 performs a processing 201 that is for determining whether the next analysis item can be analyzed. A state in which an item can be analyzed means that all conditions are satisfied under which the analysis can be conducted without any problem even when the analysis is started at the next specimen pipetting timing, for example, there are ample supplies such as reagent used for analysis; and reaction containers are usable.

When it is determined that the item can be analyzed, a processing 202 for determining whether the next analysis item will undergo dilution analysis is performed. When it is determined that the analysis item will not undergo dilution analysis, a washing operation does not need to be performed before pipetting of a diluted specimen. Accordingly, an allocation processing of standard analysis 203 is performed, and the programming processing ends.

When it is determined that the item will undergo dilution analysis, an allocation processing of dilution analysis 204 is performed. Subsequently, a processing 205 for determining whether or not washing before pipetting of a diluted specimen is required is performed. When it is determined that washing is required, it is evident that the diluted specimen accommodated in the reaction container 104 will be pipetted at least after the pipetting of a specimen from the specimen container is performed in several cycles. Consequentially, an allocation processing of washing before pipetting of a diluted specimen 206 is performed. Whether or not washing is required is determined according to, for example, the analysis item of the diluted specimen.

Figure 3:
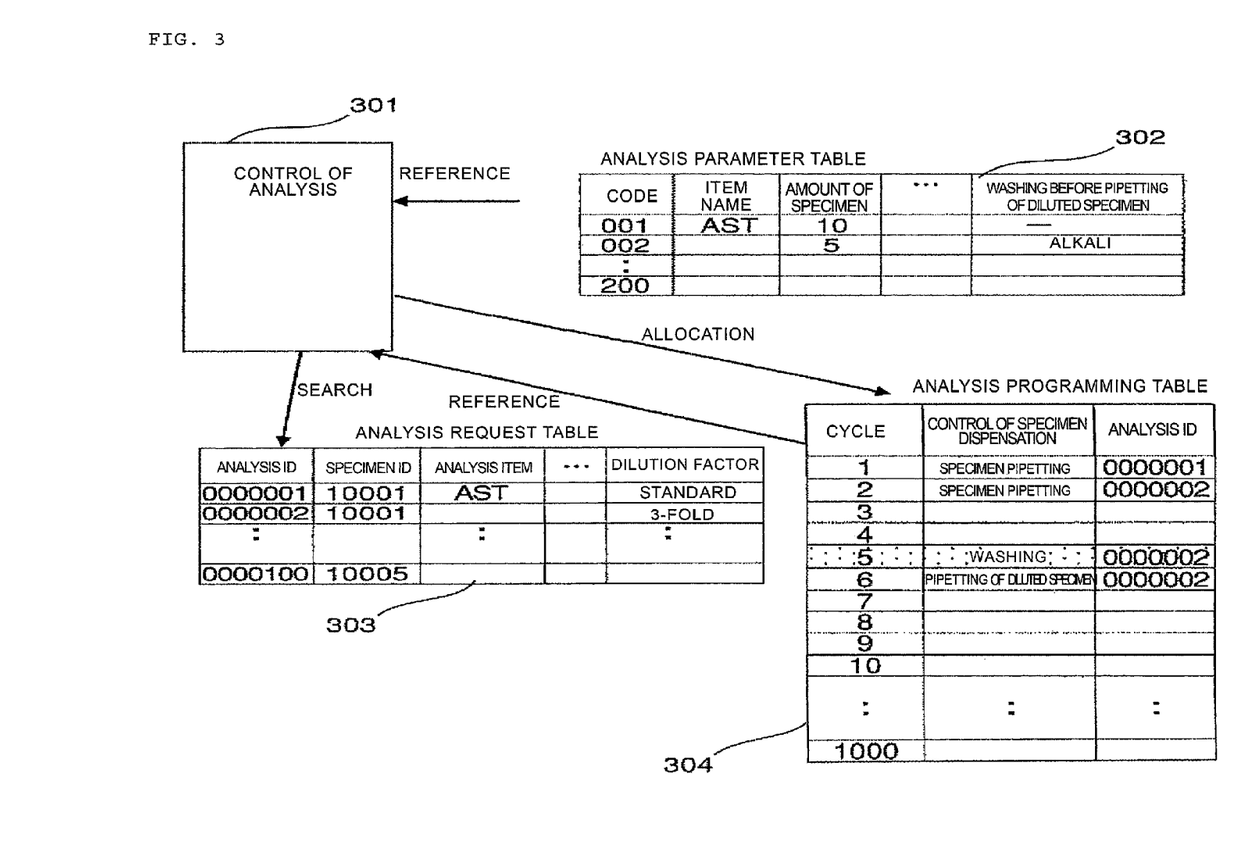
FIG. 3 is a configuration view of software for programming and executing the washing operation.

FIG. 3 is a view showing an example of software configuration regarding an allocation processing of dilution analysis 204, a processing 205 for determining whether or not washing before pipetting of a diluted specimen is required, and an allocation processing of washing before pipetting of a diluted specimen 206.

The control portion 112 includes an analysis control program 301, an analysis parameter table 302, an analysis request table 303, and an analysis programming table 304.

The analysis control program 301 searches for an analysis request, which has not yet been analyzed and has the highest priority, from the analysis request table 303, and determines the analysis request for the next analysis. The analysis request includes information about a dilution factor that shows whether there is a request for performing dilution analysis. In the case of the dilution analysis, the program allocates control of specimen pipetting to a predetermined cycle of the analysis programming table 304.

Subsequently, with reference to the analysis parameter table 302, the analysis control program 301 determines whether the next analysis item to be measured requires washing before pipetting of a diluted specimen. When it is determined that the washing before pipetting of a diluted specimen is required, the program allocates control of washing to a predetermined cycle of the analysis programming table 304. Herein, the cycle number between the pipetting of a specimen and pipetting of a diluted specimen is preset for each analyzer.

With reference to the analysis programming table 304, the analysis control program 301 executes the allocated control processing in each cycle.

In control of washing, the volume of a detergent to be used may be determined based on the maximum pipetting volume of the nozzle. However, in order to reduce consumption of the detergent, the volume of the detergent may be determined based on the pipetting volume of the diluted specimen of each item. Furthermore, the washing is not limited to washing with a detergent, and the analyzer may be controlled so as to reduce the volume of water coming into the nozzle by drying the nozzle tip.

An example of programming/execution of aforementioned control of washing before pipetting of a diluted specimen will be described.

For example, when an analysis request of analysis ID 0000002 is programmed from a second cycle, first, control of specimen pipetting is allocated to the second cycle of the analysis programming table 304, and control of pipetting of a diluted sample is allocated to a sixth cycle thereof. When the analysis parameter table 302 is referred to, it is understood that, for the analysis item of analysis ID 0000002, washing using an alkaline detergent is required as the washing before pipetting of a diluted sample. Therefore, control of washing is allocated to a fifth cycle of the analysis programming table 304. For example, provided that the pipetting volume of the diluted specimen of the analysis item of analysis ID 0000002 is 10 µL, the inside and outside of the specimen nozzle are washed by using 10 µL of an alkaline detergent. The analysis ID 0000002 and the specimen ID 10001 have the same ID. Therefore, when a pipetting process of a high-concentration specimen not being diluted and a pipetting process of a low-concentration sample diluted by the analyzer are consecutively performed, from the analysis programming table, a fact that the analyzer is programmed such that washing with a detergent is performed between the pipetting process of a high-concentration specimen and the pipetting process of a low-concentration specimen is read out. Herein, "consecutively" means that the specimen nozzle may actually perform pipetting operation continuously, regardless of whether or not there is an empty cycle between cycles. The washing with a detergent is desirably allocated to a cycle that is immediately before a cycle of performing the pipetting of a diluted specimen as shown in this example.

In this example, the washing with a detergent performed between the same specimens was described. However, needless to say, the washing with a detergent may also be performed between different specimens, in the same manner as the washing with a detergent performed between the same specimens.

Figure 4:
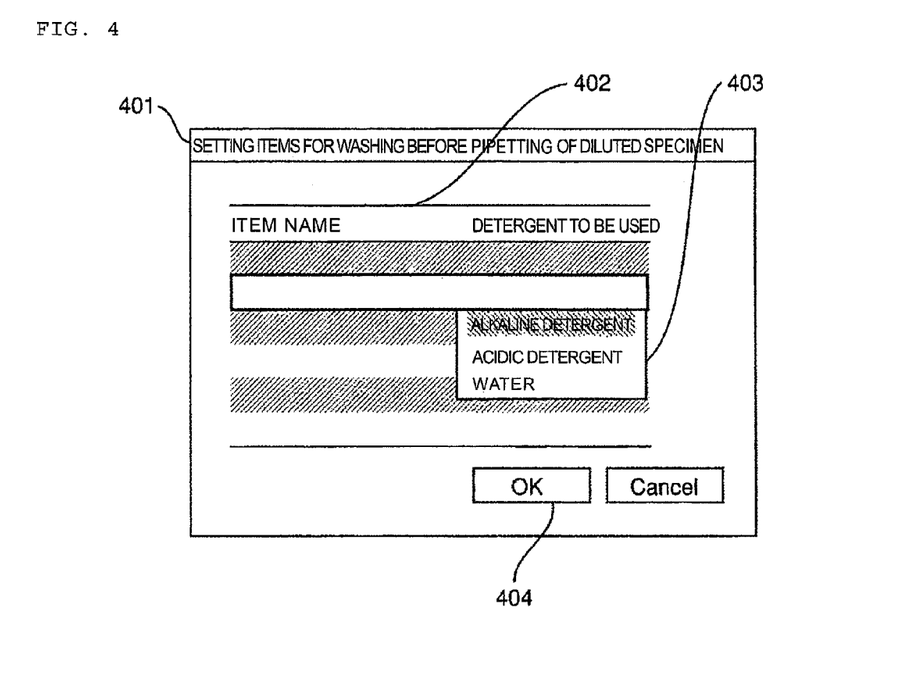
FIG. 4 is an example of a screen for setting or changing items regarding whether or not washing is performed before pipetting of a diluted specimen.

FIG. 4 is an example of a screen for setting or changing items regarding whether or not washing is performed before the pipetting of a diluted specimen.

The control portion 112 displays a screen for setting washing before pipetting of a diluted specimen 401. The screen for setting washing before pipetting of a diluted specimen 401 includes a detergent setting list 402 that displays the name of item and the type of detergent used before the pipetting of a diluted specimen when dilution analysis is performed for the item. Accordingly, if the detergent setting list 402 is used, it is possible to select the type of detergent used in washing processing for each analysis item. When an item is selected, the detergent setting list 402 displays a detergent list 403 displaying detergents that can be set, and one detergent can be selected from the list. In this example, only one detergent can be selected. However, the screen may be made such that a plurality of detergents can be selected for a single item, or the number of times of washing can be specified.

The screen for setting washing before pipetting of a diluted specimen 401 includes an OK button 404. By pressing down the button, detergent information can be stored. The set detergent information is reflected to the analysis parameter table 302.

Figure 5:
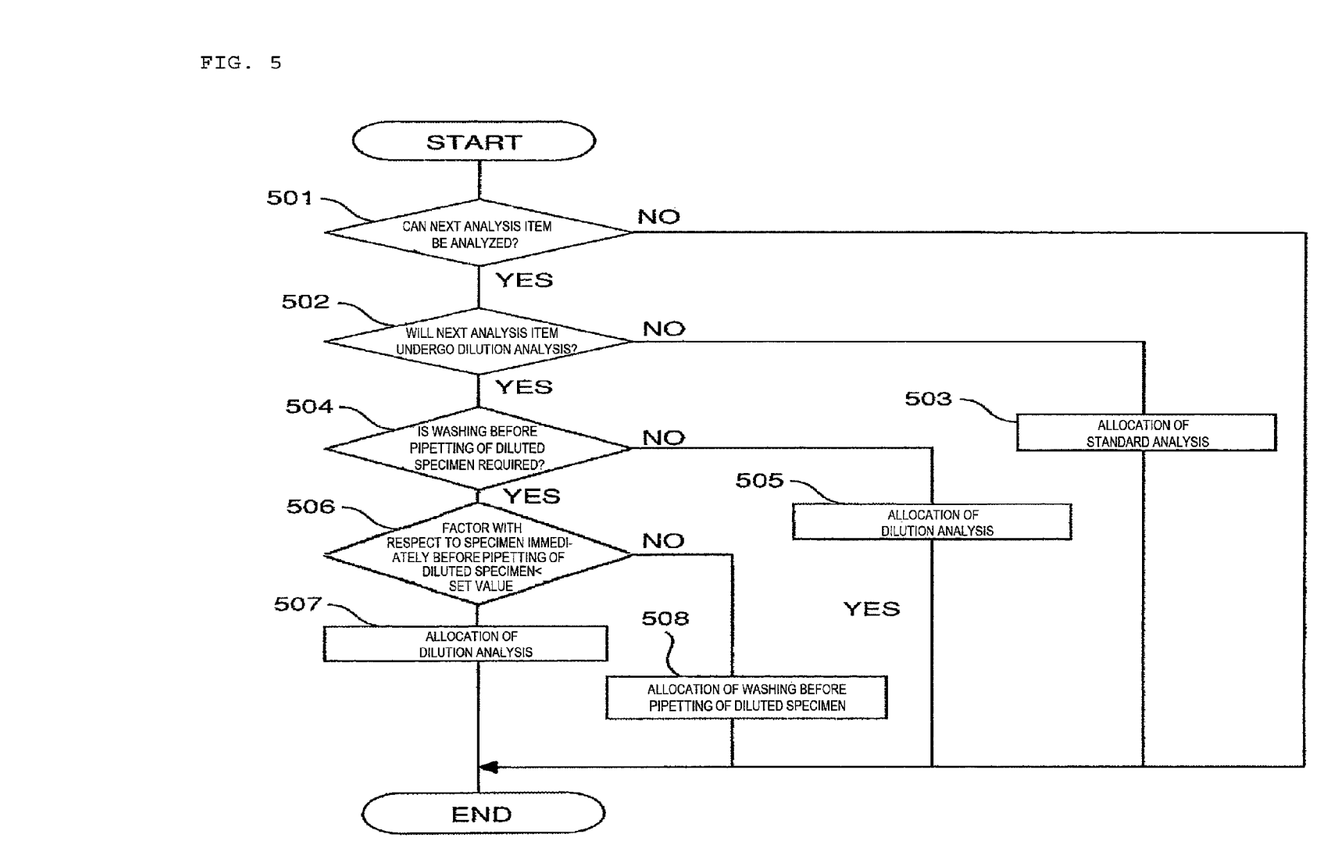
FIG. 5 is a processing flow for programming the washing operation before pipetting of a diluted specimen according to a ratio of dilution factor.

FIG. 5 shows an example of the flow of a processing of programming a washing operation that is performed when a ratio between a factor of the preceding specimen pipetting and a factor of the pipetting of a diluted specimen is equal to or greater than a certain value.

First, the control portion 112 performs a processing 501 for determining whether the next analysis item can be analyzed. A state in which an item can be analyzed means that all conditions are satisfied under which the analysis can be conducted without any problem even when the analysis is started at the next specimen pipetting timing, for example, there are ample supplies such as reagent used for analysis; and reaction containers are usable.

When it is determined that the analysis item can be analyzed, a processing 502 for determining whether the next analysis item will undergo dilution analysis is performed. When it is determined that the analysis item will not undergo dilution analysis, the washing operation does not need to be performed before the pipetting of a diluted specimen. Consequently, an allocation processing of standard analysis 503 is performed, and the programming processing ends. When it is determined that the analysis item will undergo dilution analysis, a processing 504 for determining whether or not washing before the pipetting of a diluted specimen is required is performed. When it is determined that washing is not required, an allocation processing of dilution analysis 505 is performed.

In contrast, when it is determined that washing is required, a ratio between a diluted specimen pipetting processing to be allocated a and a dilution factor of a specimen pipetted immediately before the pipetting process are compared.

At this time, when a result of "dilution factor of diluted specimen pipetting process to be allocated/dilution factor of specimen pipetted immediately before the aforementioned pipetting process<set value" is obtained by a processing for determining ratio of dilution factor 506, it is determined that the washing processing before the pipetting of a diluted specimen is not required, and an allocation processing of dilution analysis 507 is performed.

In contrast, when it is found that the ratio of dilution factor is equal to or greater than a set value by the processing for determining the ratio of dilution factor 506, this shows the concentration ratio of the diluted specimen is high. Therefore, it is determined that contamination occurs, and allocation of washing before pipetting of diluted specimen 508 is performed.

Figure 6:
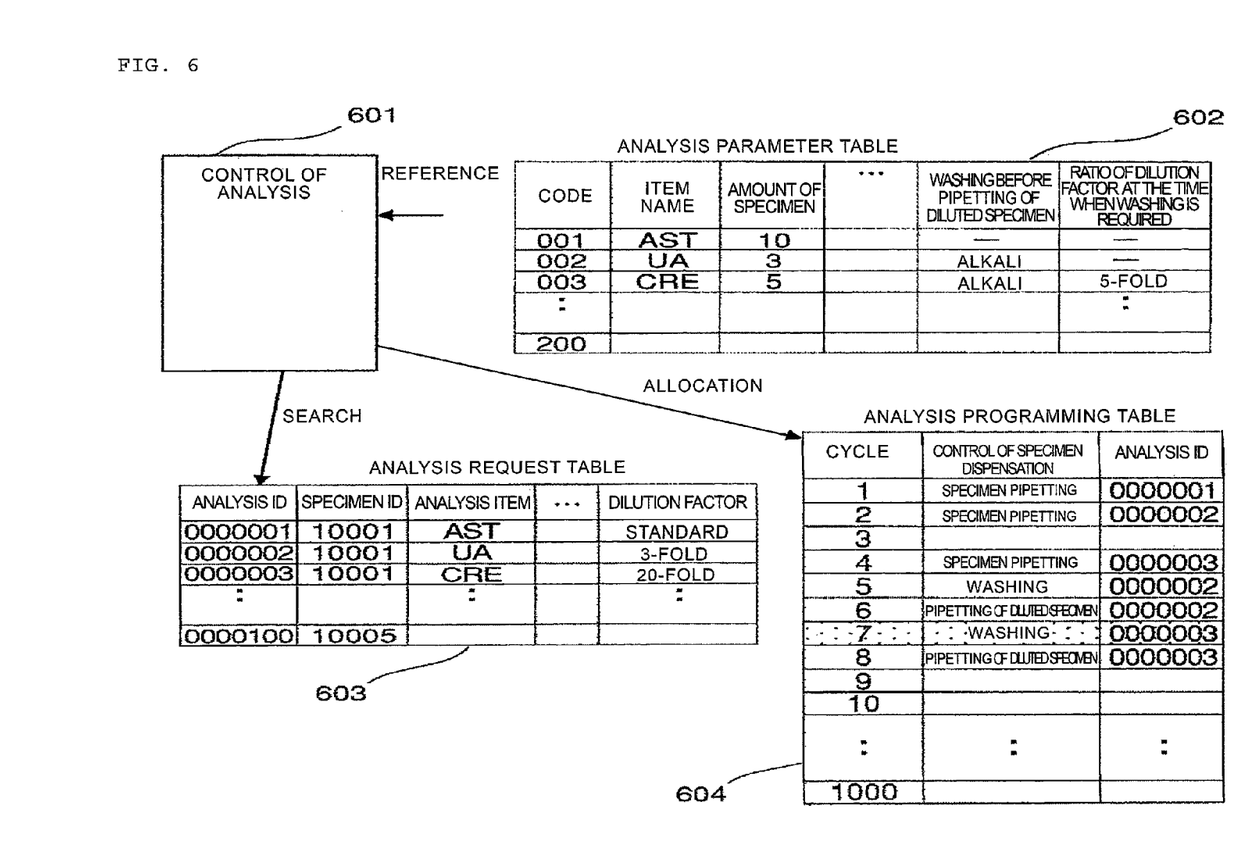
FIG. 6 is a configuration view of software for programming and executing the washing operation according to a ratio of dilution factor.

FIG. 6 is a view showing an example of the configuration of software that performs a processing for programming a washing operation when a ratio between a factor of the preceding specimen pipetting and a factor of the pipetting of a diluted specimen is equal to or greater than a certain value.

A control portion 112 includes an analysis control program 601, an analysis parameter table 602, an analysis request table 603, and an analysis programming table 604.

Unlike in the configuration of software of FIG. 3, the analysis parameter table 602 includes parameters of a ratio of dilution factor at the time when washing is required.

For example, when "5" is set as the "ratio of dilution factor at the time when washing is required" for the item of code 003, if there is a request for an analysis as shown in the analysis request table 603, the control portion executes a program via the analysis control program 601 such that a table like the analysis programming 604 is created.

When specimen pipetting of analysis ID 0000002 has been allocated to cycle 2, and pipetting of a diluted specimen of analysis ID 0000002 has been allocated to cycle 6, if an attempt at allocating a pipetting process of a specimen of analysis ID 0000003 to cycle 3 is made, pipetting of a diluted specimen of cycle 6 and pipetting of a diluted specimen of cycle 7 become consecutive. In this case, the diluted specimen of analysis ID 0000002 is diluted by 3-fold, and the diluted specimen of analysis ID 0000003 is diluted by 20-fold. Consequentially, the ratio of dilution factor thereof becomes 6.7-fold. Accordingly, the item of code 003 is influenced, and the ratio of dilution factor at the time of washing is required is 5-fold, hence the aforementioned ratio exceeds this value. As a result, for analysis ID 0000003, washing needs to be performed before the pipetting of a diluted specimen, and therefore, the specimen pipetting cannot be performed in cycle 3. This is because the cycle number between the pipetting of a specimen to be diluted and the pipetting of a diluted specimen is constant. In this example, 4 cycles are set therebetween. Therefore, for analysis ID 0000003, specimen pipetting is allocated to cycle 4; washing is allocated to cycle 7; and pipetting of a diluted specimen is allocated to cycle 8. Analysis ID 0000002 and analysis ID 0000003 have the same ID as specimen ID 10001. Accordingly, when the pipetting process of the specimen diluted by the analyzer is consecutively performed between the diluted specimens derived from the same specimen, if a ratio between a dilution factor of the preceding specimen and a dilution factor of the following specimen is equal to or greater than a certain value, from the analysis programming table, a fact that the analyzer is programmed such that washing with a detergent is performed between the pipetting process of those diluted specimens is read out.

In the present invention, the set value of the dilution factor at the time of washing is required is 5. However, the value is not necessarily 5, and the analyzer may be made such that the ratio of dilution factor as the set value can be newly set.

Moreover, in FIG. 5, if a result of "YES" is obtained by the processing for determining ratio of dilution factor 506, and thus washing before pipetting of a diluted specimen is not allocated, based on the measurement result of the diluted specimen, it is determined that the specimen needs to be retested, hence retest is performed in some cases. When the retest is performed, it is desirable for the processing for determining ratio of dilution factor 506 not to be performed, and it is desirable for the processing of washing with a detergent to be performed between this processing and the preceding pipetting process. This is because the processing 506 might determine that a retest is required since the washing with a detergent was not performed. Therefore, during the measurement of the respective items, the pipetting process, which is performed immediately before the pipetting of the specimen diluted by the analyzer, is desirably stored. Furthermore, if the processing of washing with a detergent according to FIGS. 5 and 6 has not been performed, between the pipetting process of a specimen to be retested and the preceding pipetting process, it is desirable to perform washing with a detergent in which the specimen nozzle is washed with a predetermined detergent.

When a high-concentration specimen not being diluted and a diluted low-concentration specimen, which are derived from the same specimen, are consecutively pipetted, the analyzer can be set such that the washing processing is not performed. In this case, the analyzer may include a screen which enables a user to determine whether or not washing is performed for the same specimen. The same embodiment is applied to both the washing with a detergent described in FIGS. 5 and 6 and the washing with a detergent performed for the aforementioned retest.

Furthermore, when high-concentration specimens not being diluted that are derived from the same specimen are consecutively pipetted, or when diluted low-concentration specimens that are derived from the same specimen are consecutively pipetted, it is desirable not to perform the processing of washing with a detergent between the pipetting process. This is because reduction in throughput caused by the processing of washing with a detergent can be inhibited. Moreover, when a ratio between a dilution factor of a preceding specimen and a dilution factor of a following specimen is less than a certain value, it is desirable not to perform the processing of washing with a detergent between the pipetting process of these diluted specimens. This is because reduction in throughput caused by the processing of washing with a detergent can be inhibited.

In addition, the present invention can be applied to the case of preparing diluted specimen beforehand, although such an embodiment is not described in the present example. In this case, when the factor between diluted specimens is equal to or greater than a certain value, the washing processing may be performed. To summarize, the analyzer includes means for making it possible to set the analyzer not to perform the washing processing, when the pipetting process of the same specimen is consecutively performed even if the condition for performing the processing of washing with a detergent among, several types of washing processing is satisfied.

Figure 7:
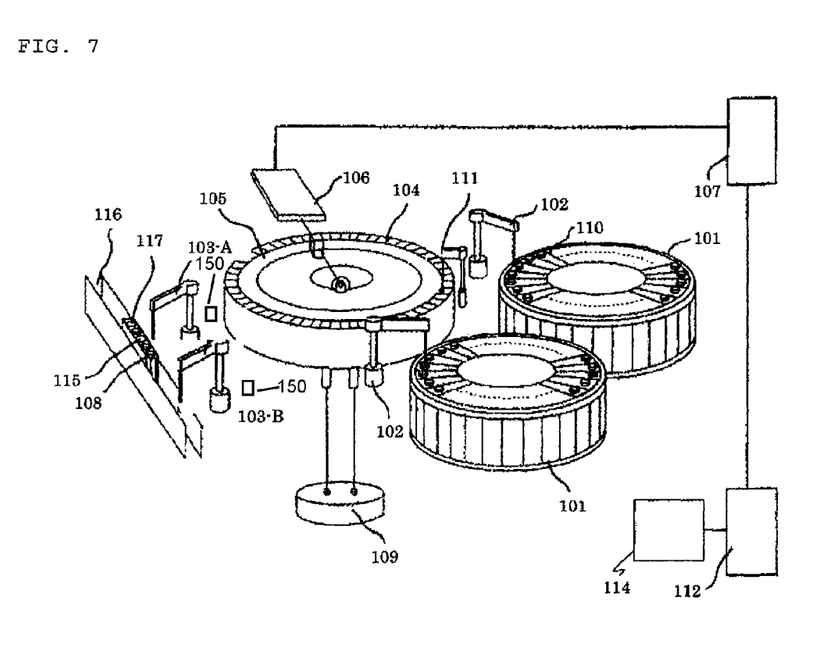
FIG. 7 is a view schematically showing overall configuration of an automated analyzer according to an embodiment of the present invention.

FIG. 7 is a view showing the overall configuration of an automated analyzer according to a second embodiment. FIG. 7 is different from FIG. 1 in the respect that the analyzer includes a plurality of sample dispensing pipetters 103. As shown in FIG. 7, the analyzer includes a sample dispensing pipetter 103-A and a sample dispensing pipetter 103-B.

The automated analyzer of the second embodiment is mainly configured with a reagent system that includes the reagent dispensing pipetter 102 provided in the vicinity of each of two reagent disks 101 and two reagent disks 101 as reagent container storage portions; a sample system that includes the sample dispensing pipetter 103-A (specimen nozzle A) and the sample dispensing pipetter 103-B (specimen nozzle B); a reaction system that includes the reaction disk 105 including the reaction containers' 104; a measurement system that includes the multi-wavelength photometer 106 and the analog/digital (A/D) converter 107; and an operation control system that includes the control portion 112 and the display input portion 114.

The rack 115 equipped with the sample containers 117 (specimen containers) is transported to the sample aspiration position 108 by the transport portion 116. The sample dispensing pipetter 103, aspirates a sample (also referred to as a "specimen") in the sample containers 117 and dispenses the sample in a predetermined volume into the reaction containers 104 held in the reaction disk 105. Furthermore, the sample dispensing pipetter 103-B aspirates the sample that has been transported to another sample dispensing position by the transport portion 116, and dispenses the sample in a predetermined volume into another reaction container 10 held in the reaction disk 105. There is a difference in time, which is taken for pipetting a sample into the reaction container 10 and then pipetting a reagent into the same reaction container 10, between the sample dispensing pipetter 103-A and the sample dispensing pipetter 103-B.

Figure 8:
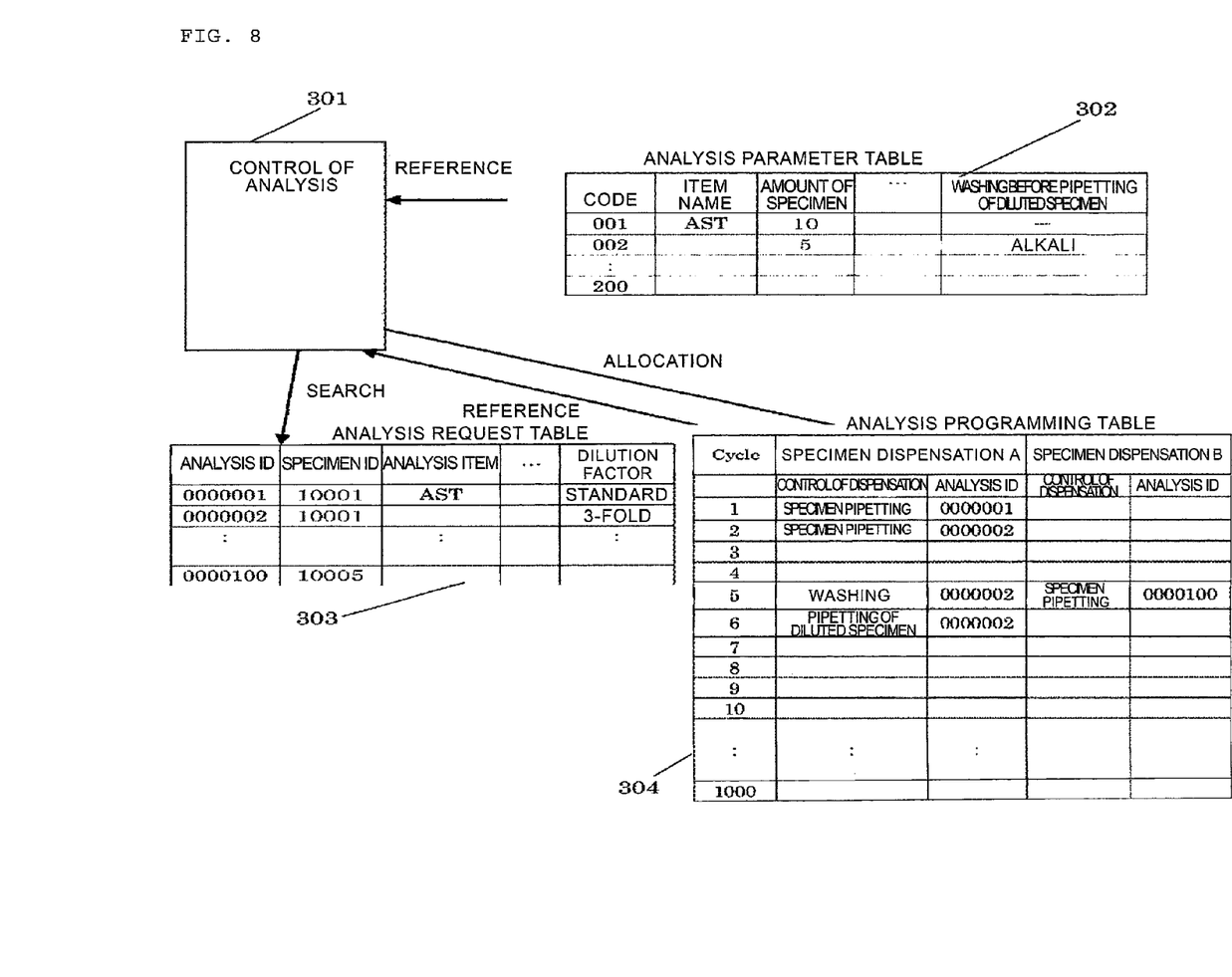
FIG. 8 is a configuration view of software for programming and executing a washing operation.

Thereafter, an example of the way the automated analyzer of FIG. 7 programs/executes control of washing before pipetting of a diluted specimen will be described by using FIG. 8. Herein, the description of the same portions as in FIG. 3 will not be repeated. FIG. 8 is different from FIG. 3 in the respect that specimen dispensation B is added to the analysis programming table. Specimen dispensation A corresponds to the sample dispensing pipetter 103 (103-A) of FIG. 1, and the specimen dispensation B corresponds to the sample dispensing pipetter 103-B newly provided. As shown in a fifth cycle, the sample dispensing pipetter 103-B can be operated in the fifth cycle. Accordingly, when a sample has been moved to the sample dispensing position of the sample dispensing pipetter 103-B, in order to measure the analysis item of analysis ID 0000100, the analyzer is controlled such that the specimen is pipetted by using the sample dispensing pipetter 103-B. In this way, even when the sample dispensing pipetter 103-A is at the timing of washing with a detergent, the sample dispensing pipetter 103-B can pipette the specimen. Consequentially, even if one of the sample dispensing pipetters is washed with a detergent, reduction in throughput of the analyzer can be inhibited.

Figure 9:
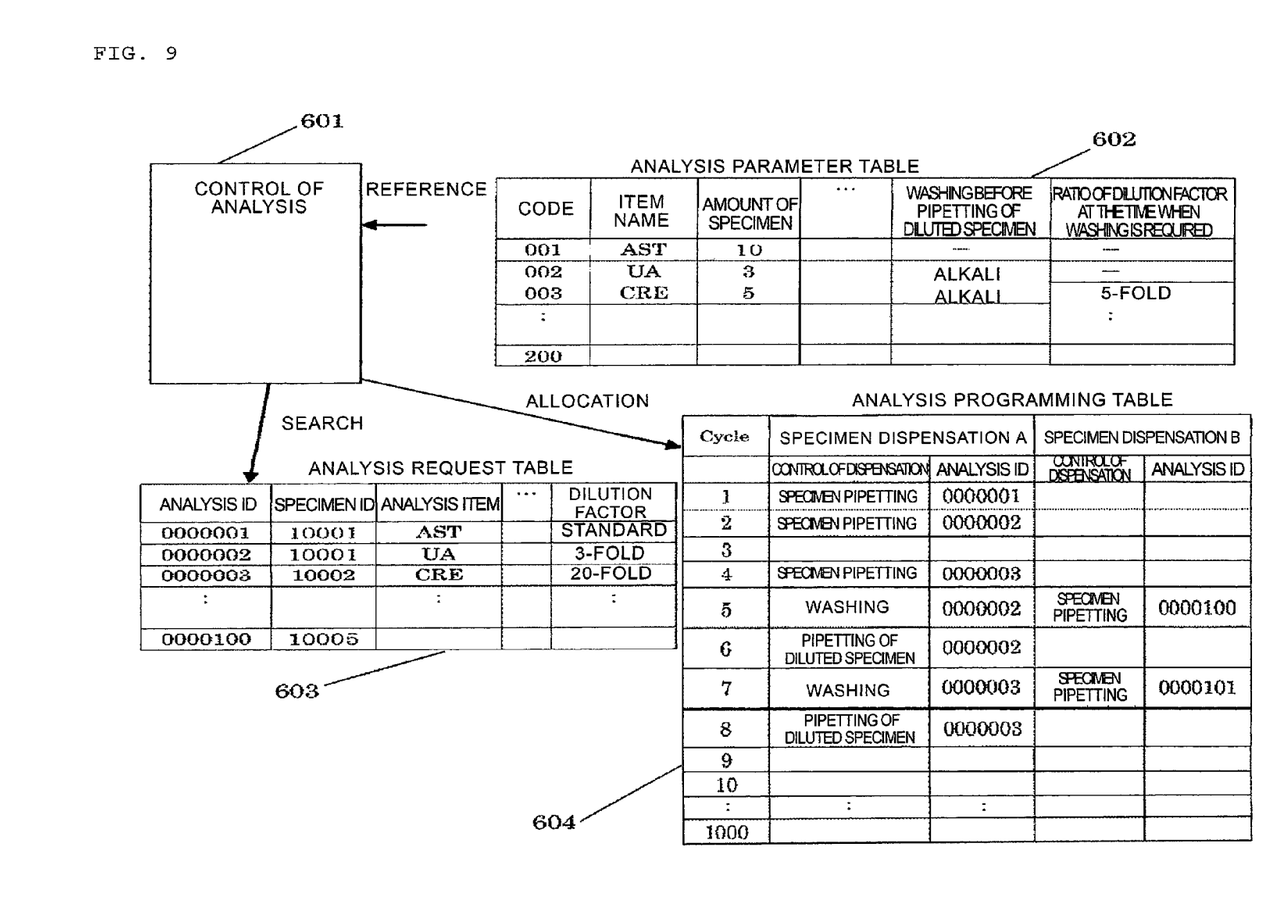
FIG. 9 is a configuration view of software for programming and executing the washing operation according to a ratio of dilution factor.

Thereafter, by using FIG. 9 showing an example of software configuration, the way the automated analyzer of FIG. 7 performs a processing for programming a washing operation when a ratio between a factor of the pipetting of a preceding specimen and a factor of the pipetting of a diluted specimen is equal to or greater than a certain value will be described. Herein, the description of the same portions as in FIG. 6 will not be repeated. FIG. 9 is different from FIG. 6 in the respect that specimen dispensation B is added to the analysis programming table. Even in this case, similarly to FIG. 8, when a sample has been moved to the sample dispensing position of the sample dispensing pipetter 103-B in cycle 7, in order to measure the analysis item of analysis ID 0000101, the analyzer is controlled such that the specimen is pipetted by using the sample dispensing pipetter 103-B. In this way, even when the sample dispensing pipetter 103-A is at the timing of washing with a detergent, the sample dispensing pipetter 103-B can pipette the specimen. Consequentially, even if one of the sample dispensing pipettors is caused to perform the processing of washing with a detergent, reduction in throughput of the analyzer can be inhibited.

Similarly, even when the sample dispensing pipettor 103-B also performs a function of pipetting a specimen diluted by the analyzer, while the sample dispensing pipettor 103-B is being washed with a detergent, the sample dispensing pipettor 103-A can pipette the specimen.

As described in the second embodiment, because the analyzer includes a second specimen nozzle for pipetting a specimen from a specimen container accommodating the specimen, and the second specimen nozzle pipettes the specimen in the cycle of performing a processing of washing with a detergent, the reduction in throughput of the analyzer can be inhibited.

Up to now, embodiments of the present invention have been described. According to the present invention, it is possible to effectively reduce contamination of a diluted low-concentration specimen that results from a high-concentration specimen not being diluted.

REFERENCE SIGNS LIST 101 reagent disk
102 reagent dispensing pipettor
103 sample dispensing pipettor
103-1 reagent dispensing pipettor A
103-2 reagent dispensing pipettor B
104 reaction container
105 reaction disk
106 multi-wavelength photometer
107 analog/digital (A/D) converter
108 sample aspiration position
109 thermostatic bath
110 reagent container
111 stirring device
112 control portion
113 emergency rack slot
114 display input portion
115 rack
116 transport portion
117 sample container
201,501 processing for determining whether analysis can be performed
202,502 processing for determining whether analysis is dilution analysis
203,503 allocation processing of standard analysis
204 allocation processing of dilution analysis
205,504 processing for determining whether or not washing before pipetting of diluted specimen is required
206 allocation processing of washing before pipetting of diluted specimen
301,601 analysis control program
302,602 analysis parameter table
303,603 analysis request table
304,604 analysis programming table
401 screen for setting washing before pipetting of diluted specimen
402 detergent setting list
403 detergent list
404 OK button
505 allocation processing of dilution analysis
506 processing for determining ratio of dilution factor

The invention claimed is:

1. An automated analyzer comprising:
a specimen nozzle configured to pipette a specimen from a specimen container accommodating the specimen, of a plurality of specimen containers, and dispense the specimen into a reaction container, of a plurality of reaction containers, and pipette a diluted specimen, which has been diluted by a diluent, and dispense the diluted specimen into another reaction container;
a washing mechanism configured to wash the specimen nozzle with a predetermined detergent;
a reagent nozzle configured to dispense a diluent into a reaction container containing a specimen;
a photometer configured to measure an absorbance of a mixture of a specimen and a reagent in a reaction container;
a control unit connected to the specimen nozzle, washing mechanism, reagent nozzle, and photometer,
wherein the control unit is programmed to:
control the specimen nozzle to pipette a specimen from the specimen container and dispense the specimen into the reaction container, determine whether the specimen requires dilution, upon determination that the specimen requires dilution, control the reagent nozzle to dispense a diluent into the reaction container accommodating the specimen, determine whether washing of the specimen nozzle by the washing mechanism is required based on whether the specimen pipetted by the specimen nozzle and the diluted specimen that is to be pipetted by the specimen nozzle consecutively are to be pipetted for the same specimen and based on a ratio between a dilution factor of an immediately preceding pipetted specimen and a dilution factor of a following pipetted specimen, wherein upon determination that the diluted specimen that is to be pipetted consecutively and a specimen pipetted by the specimen nozzle immediately preceding the diluted specimen that is to be pipetted consecutively is the same specimen, then control the specimen nozzle to pipette the diluted specimen that is to be pipetted consecutively from the reaction container without washing the specimen nozzle after pipetting the immediately preceding specimen, control the specimen nozzle to pipette the diluted specimen from the reaction container, and upon determination that washing of the specimen nozzle by the washing mechanism is required, control the specimen nozzle and the washing mechanism to wash the specimen nozzle with the predetermined detergent before controlling the specimen nozzle to pipette the diluted specimen from the reaction container.

2. The automated analyzer according to claim 1, further comprising an input means connected to the control unit for setting at least one type of detergent as the predetermined detergent used by the washing mechanism.

3. The automated analyzer according to claim 2, wherein the control unit is programmed to:

control the specimen nozzle to pipette a diluted specimen between diluted specimens of the same specimen, and if the ratio between a dilution factor of an immediately preceding pipetted specimen and a dilution factor of a following pipetted specimen is equal to or greater than a certain value, control the washing mechanism and the sample nozzle to wash the sample nozzle with the predetermined detergent.

4. The automated analyzer according to claim 3, further comprising an input means connected to the control unit for setting the predetermined dilution factor value.

5. The automated analyzer according to claim 1, further comprising a second specimen nozzle configured to pipette a specimen from a specimen container accommodating the specimen, wherein the control unit is programmed to control the second specimen nozzle to pipette a specimen while the washing mechanism washes the specimen nozzle.

* * * * *